(12) United States Patent
Foley et al.

(10) Patent No.: US 10,737,013 B2
(45) Date of Patent: Aug. 11, 2020

(54) PORTABLE TRANS ANAL IRRIGATION DEVICE

(71) Applicant: Hollister Incorporated, Libertyville, IL (US)

(72) Inventors: Adam J. Foley, Swords (IE); Stephen Collum, Castlebar (IE); Denise Gamblin, Leeds (GB); William K. Arnold, Gurnee, IL (US); Ruchi Seth, Libertyville, IL (US); Jerome A. Henry, Castlebar (IE)

(73) Assignee: Hollister Incorporated, Libertyville, IL (US)

( * ) Notice: Subject to any disclaimer, the term of this patent is extended or adjusted under 35 U.S.C. 154(b) by 291 days.

(21) Appl. No.: 15/323,147

(22) PCT Filed: Jul. 7, 2015

(86) PCT No.: PCT/US2015/039412
§ 371 (c)(1),
(2) Date: Dec. 30, 2016

(87) PCT Pub. No.: WO2016/007533
PCT Pub. Date: Jan. 14, 2016

(65) Prior Publication Data
US 2018/0043086 A1 Feb. 15, 2018

Related U.S. Application Data

(60) Provisional application No. 62/022,121, filed on Jul. 8, 2014.

(51) Int. Cl.
*A61M 3/02* (2006.01)
*A61M 3/06* (2006.01)

(52) U.S. Cl.
CPC .......... *A61M 3/025* (2013.01); *A61M 3/0212* (2014.02); *A61M 3/06* (2013.01); *A61M 2210/1067* (2013.01)

(58) Field of Classification Search
CPC ...... A61M 3/025; A61M 3/0212; A61M 3/06; A61M 2210/1067
See application file for complete search history.

(56) References Cited

U.S. PATENT DOCUMENTS 1,004,103 A 9/1911 Tacey
2,691,373 A 10/1954 Bried
(Continued)

FOREIGN PATENT DOCUMENTS

AT 369994 B 2/1983
DE 4114390 A1 11/1992
(Continued)

OTHER PUBLICATIONS

Urinary Incontinence Applicance, Aids and Equipment, R.N.P. Carroll, retrieved on Apr. 3, 2014 from http://link.springer.com/chapter/10.1007/978-1-4471-1461-1_6# dated Dec. 31, 1992.
(Continued)

*Primary Examiner* — Manuel A Mendez
*Assistant Examiner* — Tasnim Mehjabin Ahmed
(74) *Attorney, Agent, or Firm* — Cook Alex Ltd.

(57) ABSTRACT

A portable trans anal irrigation device has a hand-held water management unit removably connectable to an irrigation arm. The water management unit includes a water cartridge and a controller. The irrigation arm has a cone head for interfacing with the user's body.

8 Claims, 3 Drawing Sheets

(56) References Cited

U.S. PATENT DOCUMENTS

| | | | |
|---|---|---|---|
| 3,104,664 A * | 9/1963 | Ladd | A61M 3/022 604/150 |
| 3,653,377 A * | 4/1972 | Rebold | A61M 3/0275 601/160 |
| 3,854,483 A | 12/1974 | Powers | |
| 3,894,540 A | 7/1975 | Bonner, Jr. | |
| 3,934,722 A | 1/1976 | Goldberg | |
| 4,043,345 A | 8/1977 | Kramann et al. | |
| 4,109,659 A | 8/1978 | Sheridan | |
| 4,956,298 A | 9/1990 | Diekmann | |
| 5,149,326 A | 9/1992 | Woodgrift et al. | |
| 5,217,114 A | 6/1993 | Gadberry et al. | |
| 5,225,165 A | 7/1993 | Perlman | |
| 5,405,319 A | 4/1995 | Abell | |
| 5,413,561 A | 5/1995 | Fischell et al. | |
| 5,417,326 A | 5/1995 | Winer | |
| 5,868,265 A | 2/1999 | Kobayashi | |
| 5,881,774 A | 3/1999 | Utterberg | |
| 6,258,078 B1 | 7/2001 | Thilly | |
| 6,585,721 B2 | 7/2003 | Fiore | |
| 6,822,253 B1 | 11/2004 | Martin et al. | |
| 6,908,013 B2 | 6/2005 | Thomson et al. | |
| 6,984,226 B1 | 1/2006 | Abell | |
| 7,120,487 B2 | 10/2006 | Nelson | |
| 7,438,704 B1 | 10/2008 | Kawashima et al. | |
| 7,546,931 B2 | 6/2009 | Giusti | |
| 7,571,804 B2 | 8/2009 | Kjellmann Bruun et al. | |
| 7,614,514 B2 | 11/2009 | Fuchs | |
| 7,625,355 B2 | 12/2009 | Yu | |
| 7,682,353 B2 | 3/2010 | Tanghoj | |
| 7,717,284 B2 | 5/2010 | Giusti | |
| 7,748,550 B2 | 7/2010 | Cho | |
| 7,867,220 B2 | 1/2011 | Tanghoj | |
| 7,886,907 B2 | 2/2011 | Murray et al. | |
| 7,967,744 B2 | 6/2011 | Kaye et al. | |
| 8,137,309 B2 | 3/2012 | Nishtala et al. | |
| 8,172,101 B2 | 5/2012 | Giusti | |
| 8,181,778 B1 | 5/2012 | van Groningen et al. | |
| 8,230,993 B2 | 7/2012 | Tanghoej | |
| 8,282,624 B2 | 10/2012 | Tanghoej et al. | |
| 8,361,057 B2 | 1/2013 | Tanghoej et al. | |
| 8,398,615 B2 | 3/2013 | Torstensen et al. | |
| 8,434,639 B2 | 5/2013 | Markert | |
| 8,439,213 B2 | 5/2013 | Goria et al. | |
| 8,448,798 B2 | 5/2013 | Groubert | |
| 8,491,568 B2 | 7/2013 | Schertiger et al. | |
| 8,579,115 B2 | 11/2013 | Murphy et al. | |
| 8,752,722 B2 | 6/2014 | Kuhn et al. | |
| 8,863,968 B2 | 10/2014 | Giusti | |
| 9,352,318 B2 | 5/2016 | Giusti | |
| 9,422,089 B2 | 8/2016 | Wheeler | |
| 2002/0019613 A1 * | 2/2002 | Alexandersen | A61M 3/0295 604/279 |
| 2003/0073963 A1 | 4/2003 | Falconer | |
| 2004/0267198 A1 | 12/2004 | Torstensen | |
| 2006/0009732 A1 | 1/2006 | Hardy | |
| 2006/0142737 A1 | 6/2006 | Tanghoj | |
| 2006/0180585 A1 | 8/2006 | Cunningham et al. | |
| 2008/0033371 A1 | 2/2008 | Updegraff et al. | |
| 2008/0097384 A1 * | 4/2008 | Pacey | A61M 25/10 604/509 |
| 2008/0289984 A1 | 11/2008 | Raven | |
| 2009/0054876 A1 | 2/2009 | Borodulin | |
| 2009/0166361 A1 | 7/2009 | Lourenco | |
| 2010/0106236 A1 | 4/2010 | Nelson | |
| 2010/0211050 A1 | 8/2010 | Luther | |
| 2010/0324540 A1 | 12/2010 | Paulen et al. | |
| 2011/0060317 A1 | 3/2011 | Frojd | |
| 2011/0224653 A1 | 9/2011 | Torstensen | |
| 2011/0282311 A1 | 11/2011 | Nishtala | |
| 2011/0302709 A1 * | 12/2011 | Taylor | A61M 3/0208 4/443 |
| 2012/0016318 A1 | 1/2012 | Hoang et al. | |
| 2012/0179144 A1 | 7/2012 | Carleo | |
| 2012/0271281 A1 | 10/2012 | Schertiger | |
| 2013/0068767 A1 | 3/2013 | Fraser et al. | |
| 2013/0134123 A1 | 5/2013 | Fraser | |
| 2013/0161344 A1 | 6/2013 | Park et al. | |
| 2013/0175363 A1 * | 7/2013 | Dobias | B05B 9/0861 239/308 |
| 2013/0218136 A1 | 8/2013 | Tanghoej et al. | |
| 2013/0289537 A1 | 10/2013 | Schertiger | |
| 2013/0292286 A1 | 11/2013 | Van Groningen | |
| 2014/0012191 A1 * | 1/2014 | Iparraguirre | A61J 1/2093 604/87 |
| 2014/0018775 A1 * | 1/2014 | Swords | A61M 31/00 604/514 |
| 2014/0262860 A1 | 9/2014 | Hagel | |
| 2014/0263436 A1 | 9/2014 | Gelov et al. | |
| 2014/0360896 A1 | 12/2014 | Torstensen | |
| 2016/0016703 A1 | 1/2016 | Muhlemann | |
| 2016/0023818 A1 | 1/2016 | Gelov et al. | |
| 2016/0059999 A1 | 3/2016 | Fraser et al. | |
| 2016/0228872 A1 | 8/2016 | Giusti | |

FOREIGN PATENT DOCUMENTS

| | | |
|---|---|---|
| DE | 20117438 U1 | 3/2002 |
| DE | 10213411 A1 | 10/2003 |
| DE | 20317135 U1 | 2/2004 |
| DE | 202005008071 U1 | 7/2005 |
| DE | 202005009946 U1 | 9/2005 |
| DE | 202006013663 U1 | 11/2006 |
| DE | 202010006267 U1 | 11/2010 |
| DE | 202010007433 U1 | 7/2011 |
| DE | 202011107025 | 3/2013 |
| DE | 202011107059 | 3/2013 |
| DE | 102013014483 A1 | 6/2014 |
| EP | 0041487 A | 12/1981 |
| EP | 0134630 A | 3/1985 |
| EP | 0861639 A2 | 9/1998 |
| EP | 0809520 B1 | 4/1999 |
| EP | 0996542 A1 | 5/2000 |
| EP | 1051984 A2 | 11/2000 |
| EP | 1180373 A2 | 2/2002 |
| EP | 1011754 B1 | 9/2004 |
| EP | 1466645 A2 | 10/2004 |
| EP | 1392575 B1 | 9/2005 |
| EP | 1593710 A1 | 11/2005 |
| EP | 1634554 A2 | 3/2006 |
| EP | 1638856 A1 | 3/2006 |
| EP | 1246655 B1 | 5/2006 |
| EP | 1434611 B1 | 6/2006 |
| EP | 1671663 A1 | 6/2006 |
| EP | 1303243 B1 | 1/2007 |
| EP | 1752175 A1 | 2/2007 |
| EP | 1752176 A1 | 2/2007 |
| EP | 1752177 A1 | 2/2007 |
| EP | 1039858 B1 | 5/2007 |
| EP | 1491223 B1 | 5/2007 |
| EP | 1878461 A1 | 1/2008 |
| EP | 1897579 A1 | 3/2008 |
| EP | 1897580 A1 | 3/2008 |
| EP | 1946785 A1 | 7/2008 |
| EP | 1946786 A1 | 7/2008 |
| EP | 1372755 B1 | 8/2008 |
| EP | 0915715 B1 | 9/2008 |
| EP | 1531885 B1 | 10/2008 |
| EP | 1977778 A1 | 10/2008 |
| EP | 1982741 A2 | 10/2008 |
| EP | 1514572 B1 | 12/2008 |
| EP | 2027832 A2 | 2/2009 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2035292 B1 | 5/2010 |
| EP | 2251454 A2 | 11/2010 |
| EP | 2468326 A1 | 12/2010 |
| EP | 2211937 B1 | 7/2011 |
| EP | 2125070 B1 | 4/2012 |
| EP | 2452706 A2 | 5/2012 |

(56) References Cited

FOREIGN PATENT DOCUMENTS

| | | |
|---|---|---|
| EP | 2468319 A1 | 6/2012 |
| EP | 2005981 B1 | 9/2012 |
| EP | 1909864 B1 | 10/2012 |
| EP | 2504054 A1 | 10/2012 |
| EP | 2515985 A1 | 10/2012 |
| EP | 2158926 B1 | 5/2013 |
| EP | 2596831 A2 | 5/2013 |
| EP | 2242696 B1 | 6/2013 |
| EP | 2617316 A2 | 7/2013 |
| EP | 2638927 A2 | 9/2013 |
| EP | 2671601 A1 | 11/2013 |
| EP | 2671602 A1 | 12/2013 |
| EP | 2679259 A1 | 1/2014 |
| EP | 2679260 A1 | 1/2014 |
| EP | 2679261 A1 | 1/2014 |
| EP | 2682069 A1 | 1/2014 |
| EP | 2686054 A1 | 1/2014 |
| EP | 2703019 A1 | 3/2014 |
| EP | 2416819 B1 | 8/2014 |
| EP | 1752174 B1 | 9/2014 |
| EP | 2774648 A1 | 9/2014 |
| EP | 2576374 B1 | 9/2016 |
| FR | 2717676 A1 | 9/1995 |
| GB | 2031735 A | 4/1980 |
| GB | 2033231 A | 5/1980 |
| GB | 2322079 A | 8/1998 |
| GB | 2496900 A | 5/2013 |
| JP | 2001025473 | 1/2001 |
| KR | 20110101674 | 7/2012 |
| WO | WO 96-08219 A1 | 3/1996 |
| WO | WO 96-25188 A1 | 8/1996 |
| WO | WO 96-31250 A1 | 10/1996 |
| WO | WO 97-15335 A1 | 5/1997 |
| WO | WO 97-26937 A1 | 7/1997 |
| WO | WO 97-41811 A1 | 11/1997 |
| WO | WO 97-49441 A1 | 12/1997 |
| WO | WO 98-11932 A1 | 3/1998 |
| WO | WO 98-19729 A1 | 5/1998 |
| WO | WO 98-20722 A2 | 5/1998 |
| WO | WO 98-23312 A1 | 6/1998 |
| WO | WO 99-30652 A1 | 6/1999 |
| WO | WO 99-30761 A1 | 6/1999 |
| WO | WO 99-42155 A2 | 8/1999 |
| WO | WO 99-59656 A1 | 11/1999 |
| WO | WO 00-16843 A1 | 3/2000 |
| WO | WO 00-30575 A1 | 6/2000 |
| WO | WO 00-47494 A1 | 8/2000 |
| WO | WO 01-43807 A1 | 6/2001 |
| WO | WO 01-49345 A1 | 7/2001 |
| WO | WO 01-60255 A1 | 8/2001 |
| WO | WO 02-07668 A1 | 1/2002 |
| WO | WO 02-13887 A1 | 2/2002 |
| WO | WO 02-060361 A2 | 8/2002 |
| WO | WO 02-074363 A2 | 9/2002 |
| WO | WO 02-080843 A2 | 10/2002 |
| WO | WO 03-001994 A1 | 1/2003 |
| WO | WO 03-008028 A2 | 1/2003 |
| WO | WO 03-008029 A2 | 1/2003 |
| WO | WO 03-022561 A1 | 3/2003 |
| WO | WO 03-030967 A1 | 4/2003 |
| WO | WO 03-030968 A1 | 4/2003 |
| WO | WO 03-030969 A1 | 4/2003 |
| WO | WO 03-045487 A2 | 6/2003 |
| WO | WO 03-061732 A2 | 7/2003 |
| WO | WO 03-063668 A1 | 8/2003 |
| WO | WO 03-092779 A1 | 11/2003 |
| WO | WO 03-097237 A2 | 11/2003 |
| WO | WO 2004-006993 A1 | 1/2004 |
| WO | WO 2004-021890 A1 | 3/2004 |
| WO | WO 2004-032750 A1 | 4/2004 |
| WO | WO 2004-035123 A1 | 4/2004 |
| WO | WO 2004-050155 A1 | 6/2004 |
| WO | WO 2004-054446 A1 | 7/2004 |
| WO | WO 2004-060259 A2 | 7/2004 |
| WO | WO 2004-103153 A2 | 12/2004 |
| WO | WO 2004-112712 A2 | 12/2004 |
| WO | WO 2005-003725 A2 | 1/2005 |
| WO | WO 2005-004964 A1 | 1/2005 |
| WO | WO 2005-004970 A1 | 1/2005 |
| WO | WO 2005-014055 A2 | 2/2005 |
| WO | WO 2005-032617 A2 | 4/2005 |
| WO | WO 2006-005349 A1 | 1/2006 |
| WO | WO 2006-010556 A1 | 2/2006 |
| WO | WO 2006-015223 A2 | 2/2006 |
| WO | WO 2006/017439 A2 | 2/2006 |
| WO | WO 2006-024205 A1 | 3/2006 |
| WO | WO 2006/044249 A2 | 4/2006 |
| WO | WO 2006/044621 A2 | 4/2006 |
| WO | WO 2006/045809 A1 | 5/2006 |
| WO | WO 2006/121183 A1 | 11/2006 |
| WO | WO 2006-135934 A2 | 12/2006 |
| WO | WO 2007/005851 A2 | 1/2007 |
| WO | WO 2007/022223 A2 | 2/2007 |
| WO | WO 2007/038988 A1 | 4/2007 |
| WO | WO 2007/050685 A2 | 5/2007 |
| WO | WO 2007/081264 A1 | 7/2007 |
| WO | WO 2007/082540 A1 | 7/2007 |
| WO | WO 2007-103995 A2 | 9/2007 |
| WO | WO 2007/106356 A2 | 9/2007 |
| WO | WO 2007/106431 A2 | 9/2007 |
| WO | WO 2007/111891 A2 | 10/2007 |
| WO | WO 2007/121137 A2 | 10/2007 |
| WO | WO 2008/024136 A1 | 2/2008 |
| WO | WO 2008/030999 | 3/2008 |
| WO | WO 2008/039910 A2 | 4/2008 |
| WO | WO 2008-048856 A2 | 4/2008 |
| WO | WO 2008-058160 A2 | 5/2008 |
| WO | WO 2008/087220 A1 | 7/2008 |
| WO | WO 2008-087221 A2 | 7/2008 |
| WO | WO 2008/089081 A1 | 7/2008 |
| WO | WO 2008/090551 A2 | 7/2008 |
| WO | WO 2008/137353 A1 | 11/2008 |
| WO | WO 2009/010975 A1 | 1/2009 |
| WO | WO 2009-015152 A1 | 1/2009 |
| WO | WO 2009/017541 A1 | 2/2009 |
| WO | WO 2009-056906 A1 | 5/2009 |
| WO | WO 2009/066163 A1 | 5/2009 |
| WO | WO 2011-023196 A1 | 8/2009 |
| WO | WO 2009-128109 A1 | 10/2009 |
| WO | WO 2009/139878 A1 | 11/2009 |
| WO | WO 2009-144028 A1 | 12/2009 |
| WO | WO 2009-153973 A1 | 12/2009 |
| WO | WO 2010/006620 A1 | 1/2010 |
| WO | WO 2010-047501 A2 | 4/2010 |
| WO | WO 2010-057208 A1 | 5/2010 |
| WO | WO 2010-077980 A1 | 7/2010 |
| WO | WO 2010-115430 A1 | 10/2010 |
| WO | WO 2010-115431 A2 | 10/2010 |
| WO | WO 2010-126586 A1 | 11/2010 |
| WO | WO 2010/130261 A1 | 11/2010 |
| WO | WO 2011/011023 | 1/2011 |
| WO | WO 2011/012323 A1 | 2/2011 |
| WO | WO 2011/019359 A1 | 2/2011 |
| WO | WO 2011/026929 A1 | 3/2011 |
| WO | WO 2011/034911 A1 | 3/2011 |
| WO | WO 2011-075581 A1 | 6/2011 |
| WO | WO 2011/079129 A1 | 6/2011 |
| WO | WO 2011-105644 A1 | 9/2011 |
| WO | WO 2011/109393 A1 | 9/2011 |
| WO | WO 2011-139498 A1 | 11/2011 |
| WO | WO 2011/147803 A1 | 12/2011 |
| WO | WO 2012/006629 A2 | 1/2012 |
| WO | WO 2012/013662 A2 | 2/2012 |
| WO | WO 2012/016179 A1 | 2/2012 |
| WO | WO 2012/016570 A2 | 2/2012 |
| WO | WO 2012/016571 A2 | 2/2012 |
| WO | WO 2012/079590 A1 | 6/2012 |
| WO | WO 2012/085107 A2 | 6/2012 |
| WO | WO 2012/110755 A2 | 8/2012 |
| WO | WO 2012-120456 A2 | 9/2012 |
| WO | WO 2012/134804 A1 | 10/2012 |
| WO | WO 2012/154946 A1 | 11/2012 |
| WO | WO 2012/156478 A1 | 11/2012 |
| WO | WO 2012-164559 A1 | 12/2012 |

(56) References Cited

FOREIGN PATENT DOCUMENTS

| | | |
|---|---|---|
| WO | WO 2012/166045 A1 | 12/2012 |
| WO | WO 2012/166967 A1 | 12/2012 |
| WO | WO 2013-026564 A1 | 2/2013 |
| WO | WO 2013-026565 A1 | 2/2013 |
| WO | WO 2013/029620 A1 | 3/2013 |
| WO | WO 2013/029621 A1 | 3/2013 |
| WO | WO 2013/029622 A1 | 3/2013 |
| WO | WO 2013/075725 A1 | 5/2013 |
| WO | WO 2013-076446 A1 | 5/2013 |
| WO | WO 2013/083137 A1 | 6/2013 |
| WO | WO 2013/090778 A1 | 6/2013 |
| WO | WO 2013/098190 A1 | 7/2013 |
| WO | WO 2013/105091 A1 | 7/2013 |
| WO | WO 2013-163364 A1 | 10/2013 |
| WO | WO 2013-182593 A1 | 12/2013 |
| WO | WO 2013/184158 A1 | 12/2013 |
| WO | WO 2014-001292 A1 | 1/2014 |
| WO | WO 2014-001313 A1 | 1/2014 |
| WO | WO 2014-001322 A1 | 1/2014 |
| WO | WO 2014/062225 A1 | 4/2014 |
| WO | WO 2014/063711 A1 | 5/2014 |
| WO | WO 2014-064414 A1 | 5/2014 |
| WO | WO 2014/074142 A1 | 5/2014 |
| WO | WO 2014/074147 A1 | 5/2014 |
| WO | WO 2014/081859 A1 | 5/2014 |
| WO | WO 2014/085597 A1 | 6/2014 |
| WO | WO 2014-089278 A1 | 6/2014 |
| WO | WO 2014/093056 A1 | 6/2014 |
| WO | WO 2014/139767 | 9/2014 |
| WO | WO 2014/140328 A1 | 9/2014 |
| WO | WO 2014/142895 A1 | 9/2014 |
| WO | WO 2014/142917 A1 | 9/2014 |
| WO | WO 2014/142923 A1 | 9/2014 |
| WO | WO 2014/142930 A1 | 9/2014 |
| WO | WO 2014/144714 | 9/2014 |
| WO | WO 2014/145211 A2 | 9/2014 |
| WO | WO 2014/147620 A1 | 9/2014 |
| WO | WO 2014/149276 A1 | 9/2014 |
| WO | WO 2014/159869 A2 | 10/2014 |
| WO | WO 2014/165046 A1 | 10/2014 |
| WO | WO 2014/176486 A1 | 10/2014 |
| WO | WO 2014/176867 A1 | 11/2014 |
| WO | WO 2015/184365 | 12/2015 |

OTHER PUBLICATIONS

International Search Report dated Oct. 16, 2015, for International Application No. PCT/US2015/0039412.

* cited by examiner

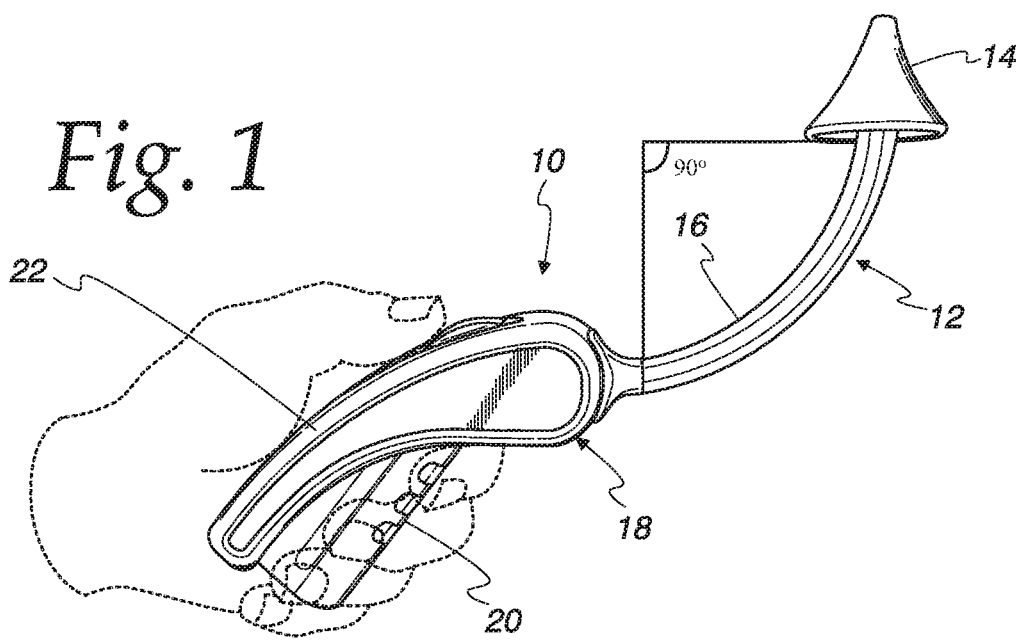
Fig. 1
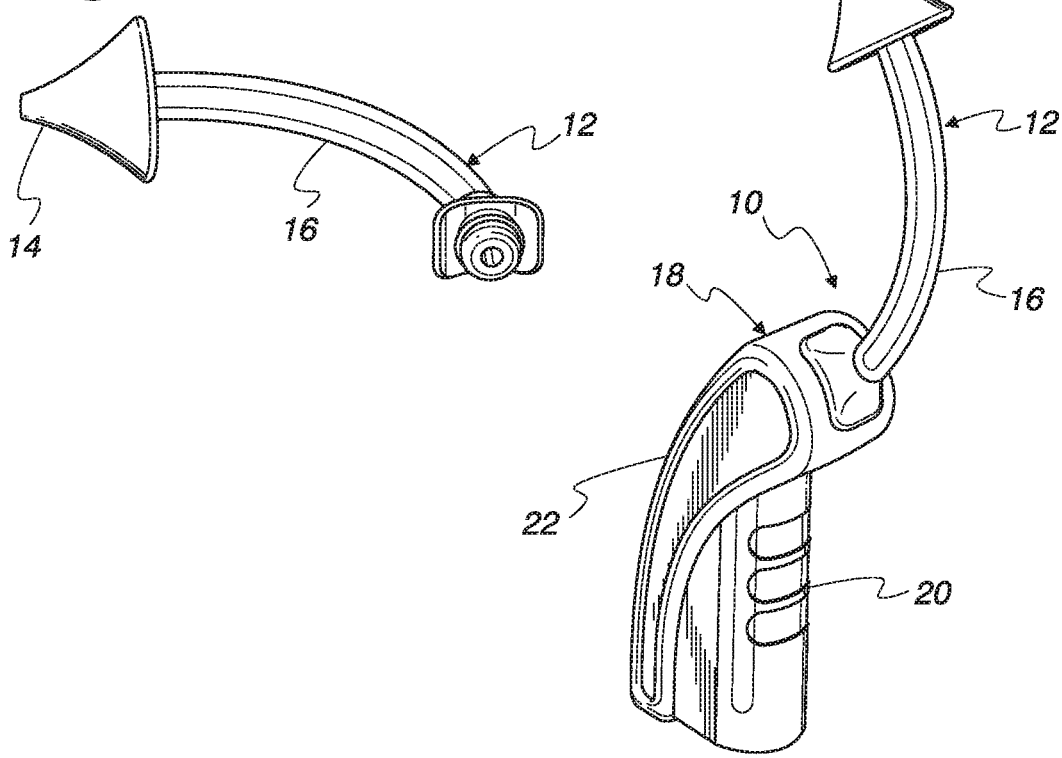
Fig. 2
Fig. 3

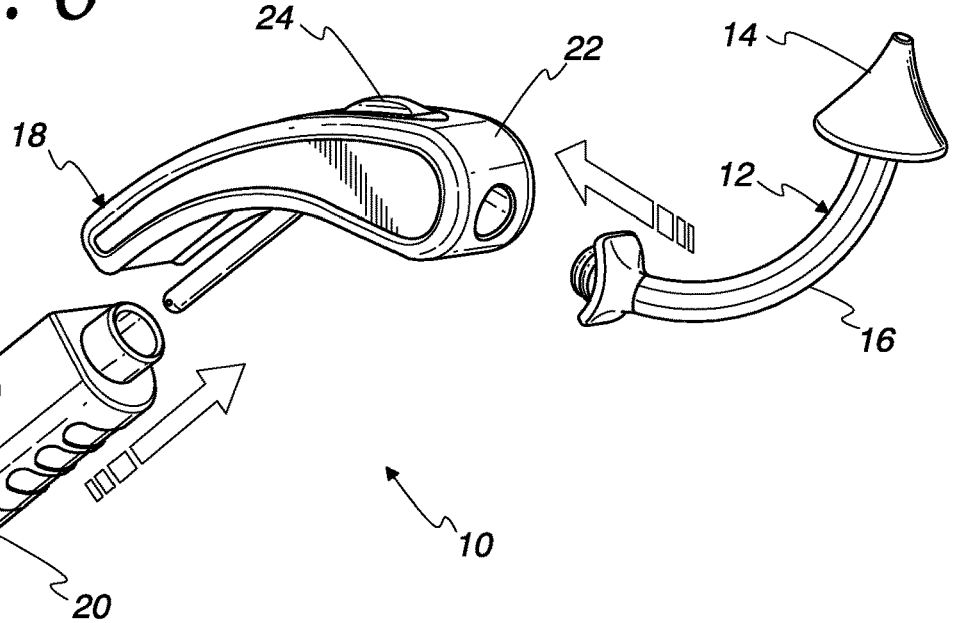
Fig. 6
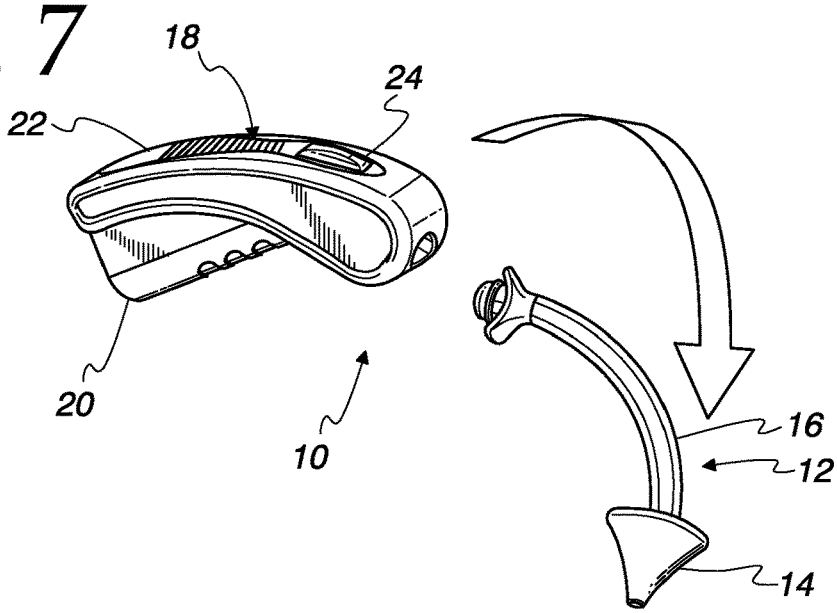
Fig. 7
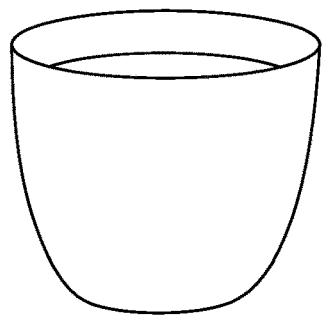

PORTABLE TRANS ANAL IRRIGATION DEVICE

CROSS REFERENCE TO RELATED APPLICATION

The present application claims priority to and the benefit of U.S. Provisional Application Ser. No. 62/022,121, filed Jul. 8, 2014, the disclosure of which is hereby incorporated herein by reference.

FIELD OF THE DISCLOSURE

The present disclosure is directed to trans anal irrigation (TAI) devices, methods and systems.

BACKGROUND

Many individuals suffering spinal cord injury (SCI) and other medical conditions (e.g. Cauda Equina, MS, Spina Bifida, and Chronic Constipation) will need to avail themselves of bowel management treatments along-side their bladder management program. In terms of SCI users the issues of independence, dexterity, ease of use are important needs that need to be addressed by a bowel management program. Users can avail of various solutions such as pharmacological, (laxatives/suppository), digital stimulation, diet control and others, with the aim of having a regular bowel management routine without constipation or fecal incontinence. This concept will focus on trans anal irrigation (TAI) which is a solution for use in bowel care. TAI is the delivery of water into the colon to flush the system of stool and create pseudo-continence for the end user. Systems currently on the market allow the user to utilize a product over the toilet or in a commode/shower chair to introduce water into the bowel through a rectal catheter (in form of rectal balloons/cones). The user will introduce an amount of water into the bowel in order to flush out stool located in the bowel passage. The user will introduce the water, wait for a period of time (30+ minutes) and allow gravity to flush the water and stool out of the body. The user can then have peace of mind through use of the product.

SUMMARY

Unlike currently available TAI solutions the present mini-irrigation product provides patients with neurogenic bowel dysfunction an on-the-go bowel irrigation solution that can help stimulate the bowels as well as clean out remaining stool and leakage. The mini-irrigation solution may benefit both community and new patients, as well as those that are using conservative interventions to manage constipation and fecal incontinence. The mini-irrigation product of the present disclosure will build confidence while providing users with an option that they can easily transport and use virtually anywhere.

The mini-irrigation product of the present disclosure addresses users such as SCI users, conservative treatments users, general users with bowel problems (e.g. constipation etc.). Such users typically have the following needs:

To always be able to completely empty a user's bowels so that no stool is remaining. The present disclosure addresses this need by providing a small volume wash-out to confirm that no stool is remaining after bowel management and to build confidence that the user will be accident free.

To be able to comfortably perform bowel management anywhere e.g., on the bed vs. in the bathroom, home vs. a public toilet, etc. The present disclosure addresses this need by providing a device that is small and can be carried easily and discreetly.

The mini-irrigation system of the present disclosure provides a small irrigation and stimulation device in a robust, easy-to-use, foldable/discreet and reusable device unlike other prior art products on the market. The mini-irrigation system can be inserted and operated with one hand. It ensures that the bowel is completely empty of the last remaining stool. It provides a complementary irrigation solution in line with conservative treatments. These consistent systems maintain a routine bowel management program and an on-the-go solution to help provide confidence throughout the day. The mini-irrigation system reduces the likelihood of accidents coming from leakage. The product may reduce the need for stimulation or suppositories. It has the potential to be inserted and held in place with one hand, suitable for people with sufficient hand function to undertake digital stimulation.

BRIEF DESCRIPTION OF THE DRAWINGS

FIG. 1 is a perspective view of the mini-irrigation device of the present disclosure.

FIG. 2 is a perspective view of the irrigation head.

FIG. 3 is a perspective view of the device of the present disclosure.

FIG. 6 is a perspective view of the set up procedure.

FIG. 7 is a perspective view of the disposal procedure.

DETAILED DESCRIPTION OF THE EMBODIMENTS

Figure 4:
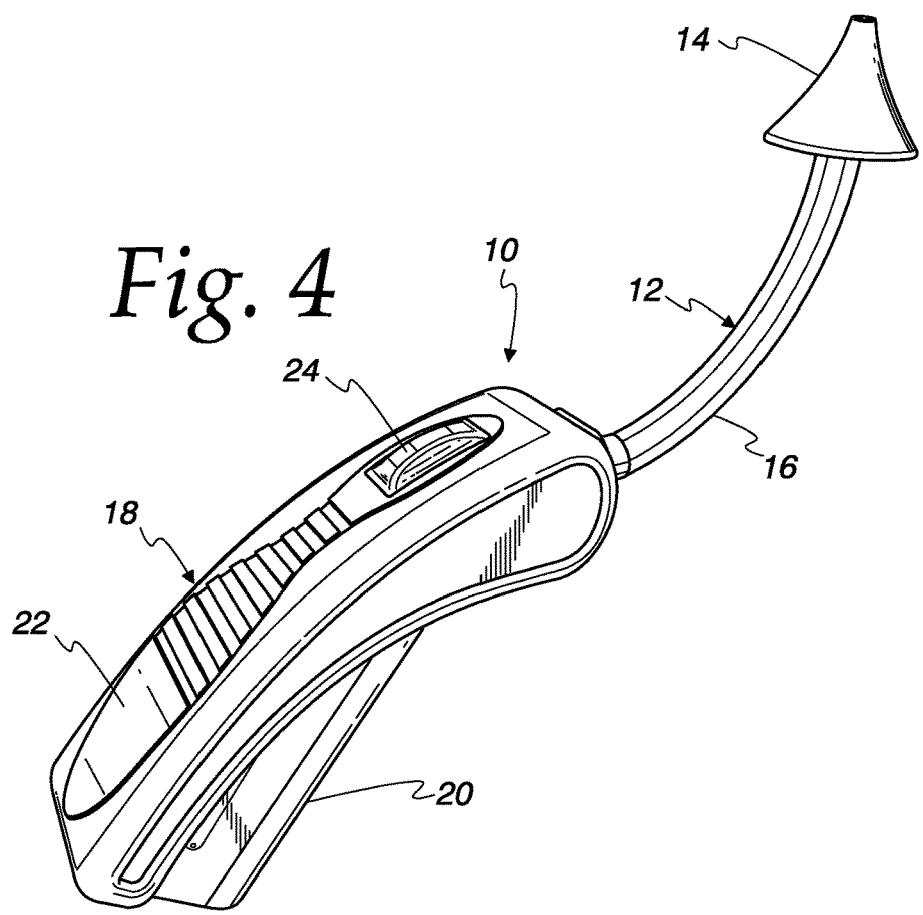
FIG. 4 is a perspective view of the device from a different angle.

FIGS. 1-4 illustrate an overview of the mini-irrigation device 10 of the present disclosure. A body interface irrigation arm is indicated generally at 12. It has a single-use, disposable, cone-shaped irrigation head 14 with easy-to-load and unload connections. Shaped tubing 16 aids in insertion. A water management unit 18 features a small volume water source in an easy-to-load and unload water cartridge 20. It loads directly into the bottom section of a controller 22. The user interface/controller 22 features an ergonomically-shaped controller unit with an easy-to-operate control button 24. The water cartridge 20 provides a wave of water from the cartridge into the body. The benefits to the end user of using this device include the following. It provides short pulsed irrigation. It has an ergonomic design which is compact and discreet for use and transport. It can be used in conjunction with conservative options. The short irrigation pulse may provide additional stimulation.

How it works is as follows. A discreet, portable, ergonomic, and easy-to-use mini-irrigation device 10 enables complete emptying of the bowel. Users with a conservative primary routine can use this solution to gain confidence that their bowel is empty. The device would be used to remove the final 10% of hard-to-remove stool, by dispensing water from a small reservoir or water cartridge 20 contained within the handle or controller 22. The user will load a disposable cone section 14 onto the head of the device. Then the cone section 14 is inserted at least partially into the rectum and the control button 24 is pressed to provide a quick wash out of the rectum. The cone section 14 is disposed of and the controller 22 and water cartridge 20 are retained for further use.

Figure 5:
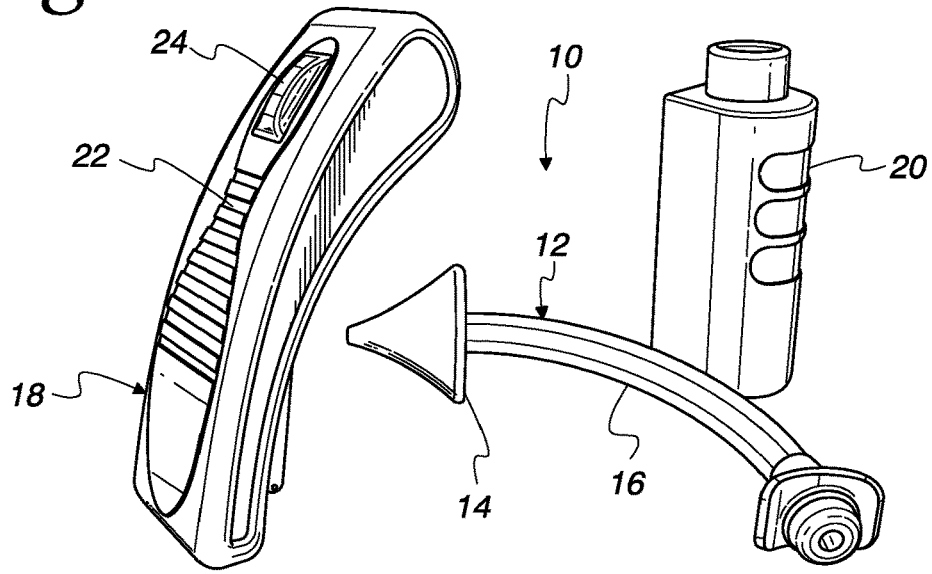
FIG. 5 is a perspective view of the separate components of the mini-irrigation device of the present disclosure.

FIGS. 5-7 detail the various components in the mini-irrigation solution. The water management unit 18 is an ergonomically-shaped unit which features a motor to draw water from the water cartridge 20, a control button 24 and a grip section or controller 22. The water cartridge 20 is about a 300+/− milliliters water compartment that is filled with water and loaded into the bottom section of the water management unit 18. The irrigation arm 12 has a cone irrigation section 14 that is loaded onto the tubing 16 and disposed of after use. The components can be separated to improve storage and transport.

During set up the user will fill the water cartridge 20 with warm water and load the cartridge 20 onto the controller 22. The irrigation arm 12 with the cone 14 is loaded onto the front of the device. The user will press the control button 24 to release water into the rectum. After use the user will remove the front cone 14 and dispose of it. In this regard the cone could be made of a flushable, water-soluble material. The water cartridge 20 and controller 22 will be retained of future use.

The controller 22 could be provided with the facility to heat the water prior to dispensing it. The system could be used to deliver medications in the irrigation fluid, e.g. suppository in liquid format soap and water enema. Flushable disposal irrigation head cones could be provided. Multi-stem head designs providing different usages and features could be used. Irrigation plus a mixture can be added to irrigate to improve performance. There could be manual evacuation and post check heads on the device. Different main body solutions may be designed to aid users with limited dexterity such as devices with large handles etc. Storage devices and cases could be provided to improve on-the-go discretion.

It should be understood that various changes and modifications to the presently preferred embodiments described herein will be apparent to those skilled in the art. Such changes and modification can be made without departing from the spirit and scope of the invention disclosed herein. For example, the volume of the water cartridge could be in a range of about 100 milliliters to about 400 milliliters. Also, the irrigation arm could be made of a flexible material to allow the user to modify the angle of insertion prior to use.

The invention claimed is:

1. An ergonomic portable rectal irrigation device comprising:

a hand-held management unit including a curved controller comprising a handle having an outer curved profile extending in a first curved direction;

a cartridge for containing a liquid, the cartridge being releasably loaded adjacent and external to a concave side of the handle's outer curved profile;

an irrigation arm having an outer curved profile extending in a second curved direction, the irrigation arm comprising an arcuate shaped tubing defining a lumen therein, the irrigation arm being removably connectable to the management unit; and when the irrigation arm is so connected to the management unit, the irrigation arm is in fluid communication with the cartridge, and the second curved direction of the outer curved profile of the irrigation arm extends in a different direction than the first curved direction of the outer profile of the handle, the irrigation arm including a head shaped for introducing liquid into a user's rectum.

2. The ergonomic portable rectal irrigation device of claim 1 wherein the cartridge is sized to contain about 300 milliliters of liquid.

3. The ergonomic portable rectal irrigation device of claim 1 wherein the controller includes a control button for releasing liquid from the cartridge to the irrigation arm.

4. The ergonomic portable rectal irrigation device of claim 1 wherein the controller is shaped to fit in the palm of a user's hand and shaped for the user's fingers to be wrapped around the cartridge, when the cartridge is engaged with the controller.

5. The ergonomic portable rectal irrigation device of claim 4 wherein the controller includes a control button for releasing liquid from the cartridge to the irrigation arm, and the controller being configured such the control button is located on the controller where a user's thumb can actuate the control button when the controller is resting in the palm of a user's hand and the user's fingers are wrapping around the cartridge.

6. The ergonomic portable rectal irrigation device of claim 1 wherein the head is cone-shaped.

7. The ergonomic portable rectal irrigation device of claim 1 wherein the arcuate shape of the irrigation arm defines an arc of about 90°.

8. The ergonomic portable rectal irrigation device of claim 1 wherein an outer surface of the cartridge includes grooves.

\* \* \* \* \*